(12) United States Patent
You et al.

(10) Patent No.: US 8,501,807 B2
(45) Date of Patent: Aug. 6, 2013

(54) PENTAERYTHRITOL DERIVATIVES (75) Inventors: Jae Won You, Seoul (KR); Chan Woo Lee, Seongnam-si (KR); Duck Hee Kim, Seoul (KR); Kil Joong Kim, Yongin-si (KR); Gae Won Nam, Yongin-si (KR); Byoung Seok Lee, Suwon-si (KR); Ih Seop Chang, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 226 days.

(21) Appl. No.: 10/599,680
(22) PCT Filed: Feb. 28, 2005
(86) PCT No.: PCT/KR2005/000554
§ 371 (c)(1), (2), (4) Date: Jun. 19, 2007
(87) PCT Pub. No.: WO2005/097718
PCT Pub. Date: Oct. 20, 2005

(65) Prior Publication Data
US 2007/0293569 A1 Dec. 20, 2007

(30) Foreign Application Priority Data
Apr. 10, 2004 (KR) .......................... 10-2004-0024704

(51) Int. Cl.
A61K 31/225 (2006.01)
(52) U.S. Cl.
USPC ........................................................ 514/547
(58) Field of Classification Search
USPC ........................................................ 514/547
See application file for complete search history.

(56) References Cited

U.S. PATENT DOCUMENTS

| | | | |
|---|---|---|---|
| 4,110,276 A | | 8/1978 | DesMarais |
| 4,766,153 A | | 8/1988 | Casciani |
| 4,767,625 A | * | 8/1988 | Mitsuno et al. ............... 424/401 |
| 5,576,470 A | | 11/1996 | Tuller et al. |
| 5,641,479 A | * | 6/1997 | Linares et al. ............. 424/70.21 |
| 5,854,201 A | | 12/1998 | Behler et al. |
| 2003/0078443 A1 | | 4/2003 | Lee et al. |

FOREIGN PATENT DOCUMENTS

| | | |
|---|---|---|
| DE | 04240153 A1 | 6/1994 |
| EP | 0163806 B1 | 12/1985 |
| EP | 1 249 846 A2 | 10/2002 |
| JP | 60-239440 A | 11/1985 |
| JP | 04-089450 A | 3/1992 |
| JP | 1992-089450 A | 3/1992 |
| JP | 2002-145734 A | 5/2002 |
| WO | 96/06824 A1 | 3/1996 |

OTHER PUBLICATIONS

Yokoyama et al. (J Wood Sci, vol. 44, pp. 421-422; 1998).*
Japanese Office Action issued in corresponding JP Application No. 2007-507236, dated Oct. 19, 2010.
European Patent Office, Search Report issued in corresponding EP Application No. 05 721 885.1, dated Mar. 19, 2012.

* cited by examiner

*Primary Examiner* — Jeffrey S. Lundgren
*Assistant Examiner* — Nelson Blakely, III
(74) *Attorney, Agent, or Firm* — Sughrue Mion, PLLC (57) ABSTRACT

Disclosed is a pentaerythritol derivative represented by the following Formula 1, which improves moisture retaining ability of the stratum corneum when applied to the skin, and shows especially high moisturizing ability even in dry conditions.

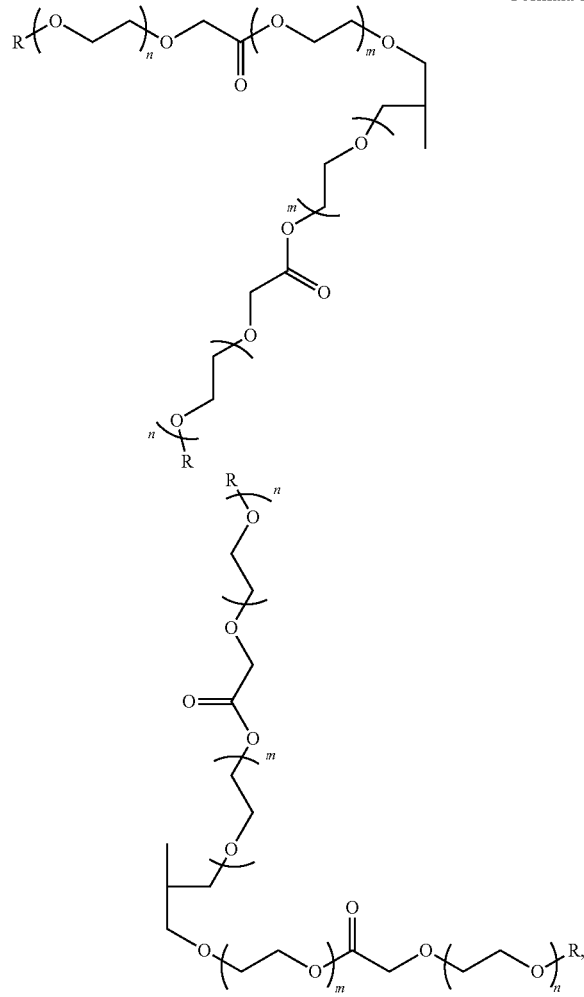

wherein R is independently saturated or unsaturated C6-C18 alkyl group; m and n are the same or different integers of which m is 0 to 10 and n is 1 to 10.

1 Claim, 3 Drawing Sheets

PENTAERYTHRITOL DERIVATIVES

This is a national sage application under 35 U.S.C. §371 of PCT/KR2005/000554 filed on Feb. 28, 2005, which claims priority from Korean patent application 10-2004-0024704 filed Apr. 10, 2004, all of which are incorporated herein by reference.

BACKGROUND OF THE INVENTION

1. Field of the Invention

The present invention relates to pentaerythritol derivatives represented by the following formula 1, which improve the moisture retaining ability of the stratum corneum when applied to the skin, and especially show high moisturizing ability even in dry conditions, to a preparation method thereof, and to a liquid crystal base containing the same.

and preventing moisture inside the skin from evaporating outside, thereby maintaining skin moistness. However, as the skin becomes aged, these functions of the stratum corneum deteriorate and the skin becomes easily dry. Moreover this tendency is increased in dry winter conditions.

Therefore, in order to improve skin dryness, numerous moisturizers have been developed. Representative examples are water-soluble moisturizers and ceramides. Because water-soluble moisturizers such as amino acid, organic acid and urea have excellent water absorbing ability, and provide moisture for the stratum corneum layer, they are used as general moisturizers. However, they show the problem that moisturizing ability decreases drastically in dry conditions of low humidity such as in winter. Further, although ceramides, as important constituents of intercellular lipid in the stratum corneum cells, have an excellent effect on enhancing skin barrier function and maintaining skin moisture, their stability

[Formula 1]

(Wherein R is the same or different, saturated or unsaturated, linear or branched alkyl groups of 1 to 24 carbon atoms having hydrogen or hydroxy group or not; m and n are the same or different integers of which m is 0 to 10 and n is 1 to 10).

2. Description of Prior Art

The stratum corneum of the skin has the functions of protecting the human body from external harmful substances, of formulation decreases when used in high content because they have low compatibility with oils used in cosmetic compositions. Therefore, ceramides have been difficult to use in substantially effective concentration.

Therefore, there is a need to develop oil-soluble moisturizers that have high moisturizing ability, thus having an excellent effect on moisture maintenance even in dry conditions, and also being easy to use in cosmetic compositions.

The present inventors have studied to develop oil-soluble moisturizers, and as a result, have developed pentaerythritol derivatives represented by the following formula 1, which show high moisturizing ability even in dry conditions, to complete the present invention.

SUMMARY OF THE INVENTION

An object of the present invention is to provide pentaerythritol derivatives represented by the following formula 1, which improve the moisture retaining ability of the stratum corneum when applied to the skin, and especially show high moisturizing ability even in dry conditions.

Another object of the present invention is to provide a method for preparing the above-mentioned pentaerythritol derivatives.

A further object of the present invention is to provide a liquid crystal base containing above-mentioned pentaerythritol derivatives.

DETAILED DESCRIPTION OF THE INVENTION

According to the present invention, pentaerythritol derivatives represented by the following formula 1 are provided:

(Wherein R is the same or different, saturated or unsaturated, linear or branched alkyl groups of 1 to 24 carbon atoms having hydrogen or hydroxy group or not; m and n are the same or different integers of which m is 0 to 10 and n is 1 to 10).

The pentaerythritol derivatives according to the present invention, as is confirmed by the Examples below, improve the water maintenance ability of the stratum corneum when applied to the skin, and especially show high moisturizing ability even in dry conditions. Further, the pentaerythritol derivatives of the invention may be combined in high content into a liquid crystal base, thereby stably forming liquid crystal.

The pentaerythritol derivatives according to the invention may be prepared by a method comprising the steps of:

(1) Synthesizing pentaerythritol derivatives by refluxing pentaerythritol, pentaerythritol ethoxylate or pentaerythritol propoxylate with carboxylic acid having ethylene glycol repeat unit (—$OCH_2CH_2O$—), in the presence of acid catalyst;

(2) Purifying the pentaerythritol derivatives prepared in step (1).

A method for preparing pentaerythritol derivatives according to the present invention may be schematized by the following reaction scheme:

[Formula 1]

[Reaction scheme 1]

Hereinafter, a method for preparing pentaerythritol derivatives according to the present invention is described in detail.

Step (1): Synthesis of pentaerythritol derivatives

As the pentaerythritol ethoxylate or pentaerythritol propoxylate in step (1), pentaerythritol ethoxylate or pentaerythritol propoxylate having 4 to 40 ethylene glycol repeat units ($-OCH_2CH_2O-$) or propylene glycol repeat units ($-OCH_2CH_2CH_2O-$) in its molecule may be employed.

In addition, as the carboxylic acid in step (1), saturated or unsaturated, linear or branched carboxylic acid of 6 to 75 carbon atoms may be employed. For example, glycolic acid ethoxylate 4-tert-butylphenyl ether, glycolic acid ethoxylate 4-nonylphenyl ether, glycolic acid ethoxylate hexyl ether, glycolic acid ethoxylate heptyl ether, glycolic acid ethoxylate octyl ether, glycolic acid ethoxylate nonyl ether, glycolic acid ethoxylate decyl ether, glycolic acid ethoxylate lauryl ether, glycolic acid ethoxylate tetradecyl ether, glycolic acid ethoxylate hexadecyl ether, glycolic acid ethoxylate stearyl ether or glycolic acid ethoxylate oleyl ether, which should not be considered to limit the scope of the present invention, may be employed.

As an organic solvent in step (1), solvent which is azeotropic distillable with water is preferred, for example, benzene, toluene, xylene, or the like may be employed. Also, the mixed solvent of these solvents with dicholoromethane, tetrahydrofuran, acetic acid ethyl, acetonitrile, chloroform, ethyl ether, trichloroethylene, dimethylformamide, or the like may be used. Further, solvent-free reaction in which organic solvent is not used is also possible.

In addition, as an acid catalyst in step (1), organic acid such as p-toluene sulfonic acid, pyridine p-toluene sulfonic acid salt or the like; or inorganic acid such as sulfuric acid, hydrochloric acid or the like may be employed. Usage equivalents may be 0.001~2, and preferably 0.01~2, because reaction slows down below 0.01, and side reaction may occur above 2.

Step (2): Purification of pentaerythritol derivatives

The pentaerythritol derivatives synthesized in step (1) may be purified by aliquoting with nonpolar solvent to remove impurities.

As nonpolar solvent in this step, examples are pentane, hexane, heptane, cyclohexane, octane, isooctane, decane, and the like, which should not be considered to limit the scope of the present invention. Usage amount of nonpolar solvent may be 30~200% based on the mass of pentaerythritol derivatives, and preferably 70~150%, because removing impurities is not easy below 70%, and the yield may be decreased above 150%.

DESCRIPTION OF THE PREFERRED EMBODIMENTS

The present invention will be described in more detail by way of the following examples. However, these examples are provided for the purpose of illustration only and should not be construed as limiting the scope of the invention, which will be apparent to one skilled in the art.

Example 1

Preparation of pentaerythritol glycolic ester ethoxylate hexyl ether (pentaerythritol hexeth-4 carboxylate)

13.6 g (100 mmol) of pentaerythritol and 110.4 g (400 mmol) of glycolic ethoxylate hexyl ether(hexeth-4 carboxylic acid) were dissolved in 2 l of benzene. To the resultant solution, 7.6 g (40 mmol) of p-toluene sulfonic acid was added and refluxed while stirring. Eliminating water with Dean-stark, the reaction was continued for 8 hours.

After the reaction was complete, the organic layer was washed twice with 1 l of water, dried with anhydrous sodium sulfate and then filtrated. After filtration, the remaining solution was distilled under reduced pressure, concentrated, and aliquoted with 100 ml of hexane to remove the hexane layer. The remaining aliquot was again distilled under reduced pressure and concentrated to obtain 93 g of pentaerythritol glycolic ester ethoxylate hexyl ether (pentaerythritol hexeth-4 carboxylate).

$^1$H-NMR (in $CHCl_3$): 4.18 (16H), 3.65 (48H), 3.44 (8H, t, J=6.9 Hz), 1.57 (8H, m), 1.26 (24H), 0.88 (12H, t, J=6.6 Hz)

Example 2

Preparation of pentaerythritol glycolic ester ethoxylate hexyl ether (pentaerythritol hexeth-6 carboxylate)

Except that 145.6 g (400 mmol) of glycolic ethoxylate hexyl ether (hexeth-6 carboxylic acid) was used instead of glycolic ethoxylate hexyl ether (hexeth-4 carboxylic acid), the same procedure described in Example 1 was performed to obtain 121.5 g of pentaerythritol glycolic ester ethoxylate hexyl ether (pentaerythritol hexeth-6 carboxylate).

$^1$H-NMR (in $CHCl_3$): 4.18 (16H), 3.66 (80H), 3.44 (8H, t, J=6.9 Hz), 1.56 (8H, m), 1.26 (24H), 0.88 (12H, t, J=6.6 Hz)

Example 3

Preparation of pentaerythritol glycolic ester ethoxylate octyl ether (pentaerythritol capreth-4 carboxylate)

Except that 121.6 g (400 mmol) of glycolic ethoxylate octyl ether (capreth-4 carboxylic acid) was used instead of glycolic ethoxylate hexyl ether (hexeth-4 carboxylic acid), the same procedure described in Example 1 was performed to obtain 104.6 g of pentaerythritol glycolic ester ethoxylate octyl ether (pentaerythritol capreth-4 carboxylate).

$^1$H-NMR (in $CHCl_3$): 4.17 (16H), 3.66 (48H), 3.45 (8H, t, J=6.9 Hz), 1.57 (8H, m), 1.26 (40H), 0.88 (12H, t, J=6.6 Hz)

Example 4

Preparation of pentaerythritol glycolic ester ethoxylate octyl ether (pentaerythritol capreth-6 carboxylate)

Except that 164.0 g (400 mmol) of glycolic ethoxylate octyl ether (capreth-6 carboxylic acid) was used instead of glycolic ethoxylate hexyl ether (hexeth-4 carboxylic acid), the same procedure described in Example 1 was performed to obtain 137.2 g of pentaerythritol glycolic ester ethoxylate octyl ether (pentaerythritol capreth-6 carboxylate).

$^1$H-NMR (in $CHCl_3$): 4.17 (16H), 3.66 (80H), 3.46 (8H, t, J=6.9 Hz), 1.57 (8H, m), 1.26 (40H), 0.87 (12H, t, J=6.6 Hz)

Example 5

Preparation of pentaerythritol glycolic ester ethoxylate lauryl ether (pentaerythritol laureth-4 carboxylate)

Except that 144.0 g (400 mmol) of glycolic ethoxylate lauryl ether (laureth-4 carboxylic acid) was used instead of glycolic ethoxylate hexyl ether (hexeth-4 carboxylic acid), the same procedure described in Example 1 was performed to obtain 121.2 g of pentaerythritol glycolic ester ethoxylate lauryl ether (pentaerythritol laureth-4 carboxylate).

$^1$H-NMR (in $CHCl_3$): 4.17 (16H), 3.66 (48H), 3.46 (8H, t, J=6.9 Hz), 1.57 (8H, m), 1.26 (72H), 0.88 (12H, t, J=6.6 Hz)

Example 6

Preparation of pentaerythritol glycolic ester ethoxylate lauryl ether (pentaerythritol laureth-6 carboxylate)

Except that 184.0 g (400 mmol) of glycolic ethoxylate lauryl ether (laureth-6 carboxylic acid) was used instead of glycolic ethoxylate hexyl ether (hexeth-4 carboxylic acid), the same procedure described in Example 1 was performed to obtain 158.5 g of pentaerythritol glycolic ester ethoxylate lauryl ether (pentaerythritol laureth-6 carboxylate).

$^1$H-NMR (in $CHCl_3$): 4.17 (16H), 3.66 (80H), 3.47 (8H, t, J=6.9 Hz), 1.57 (8H, m), 1.26 (72H), 0.88 (12H, t, J=6.6 Hz)

Example 7

Preparation of pentaerythritol glycolic ester ethoxylate lauryl ether (pentaerythritol laureth-10 carboxylate)

Except that 254.4 g (400 mmol) of glycolic ethoxylate lauryl ether (laureth-10 carboxylic acid) was used instead of glycolic ethoxylate hexyl ether (hexeth-4 carboxylic acid), the same procedure described in Example 1 was performed to obtain 218.4 g of pentaerythritol glycolic ester ethoxylate lauryl ether (pentaerythritol laureth-10 carboxylate).

$^1$H-NMR (in CHCl$_3$): 4.17 (16H), 3.67 (144H), 3.46 (8H, t, J=6.9 Hz), 1.57 (8H, m), 1.27 (72H), 0.88 (12H, t, J=6.6 Hz)

Example 8

Preparation of pentaerythritol glycolic ester ethoxylate cetyl ether (pentaerythritol ceteth-4 carboxylate)

Except that 162.4 g (400 mmol) of glycolic ethoxylate cetyl ether (ceteth-4 carboxylic acid) was used instead of glycolic ethoxylate hexyl ether (hexeth-4 carboxylic acid), the same procedure described in Example 1 was performed to obtain 138.2 g of pentaerythritol glycolic ester ethoxylate cetyl ether (pentaerythritol ceteth-4 carboxylate).

$^1$H-NMR (in CHCl$_3$): 4.17 (16H), 3.67 (48H), 3.46 (8H, t, J=6.9 Hz), 1.57 (8H, m), 1.26 (104H), 0.88 (12H, t, J=6.6 Hz)

Example 9

Preparation of pentaerythritol glycolic ester ethoxylate cetyl ether (pentaerythritol ceteth-6 carboxylate)

Except that 197.6 g (400 mmol) of glycolic ethoxylate cetyl ether (ceteth-6 carboxylic acid) was used instead of glycolic ethoxylate hexyl ether (hexeth-4 carboxylic acid), the same procedure described in Example 1 was performed to obtain 163.8 g of pentaerythritol glycolic ester ethoxylate cetyl ether (pentaerythritol ceteth-6 carboxylate).

$^1$H-NMR (in CHCl$_3$): 4.17 (16H), 3.67 (8014), 3.47 (8H, t, J=6.9 Hz), 1.57 (8H, m), 1.26 (104H), 0.87 (12H, t, J=6.6 Hz)

Example 10

Preparation of pentaerythritol glycolic ester ethoxylate cetyl ether (pentaerythritol ceteth-10 carboxylate)

Except that 268.0 g (400 mmol) of glycolic ethoxylate cetyl ether (ceteth-10 carboxylic acid) was used instead of glycolic ethoxylate hexyl ether (hexeth-4 carboxylic acid), the same procedure described in Example 1 was performed to obtain 247.4 g of pentaerythritol glycolic ester ethoxylate cetyl ether (pentaerythritol ceteth-10 carboxylate).

$^1$H-NMR (in CHCl$_3$): 4.17 (16H), 3.67 (144H), 3.47 (8H, t, J=6.9 Hz), 10.57 (8H, m), 1.26 (104H), 0.87 (12H, t, J=6.6 Hz)

Example 11

Preparation of pentaerythritol glycolic ester ethoxylate oleyl ether (pentaerythritol oleth-6 carboxylate)

Except that 216.0 g (400 mmol) of glycolic ethoxylate oleyl ether (oleth-6 carboxylic acid) was used instead of glycolic ethoxylate hexyl ether (hexeth-4 carboxylic acid), the same procedure described in Example 1 was performed to obtain 187.1 g of pentaerythritol glycolic ester ethoxylate oleyl ether (pentaerythritol oleth-6 carboxylate).

$^1$H-NMR (in CHCl$_3$): 5.64 (8H), 4.16 (16H), 3.67 (80H), 3.47 (8H, t, J=6.9 Hz), 2.02 (16H), 1.57 (8H, m), 1.27 (80H), 0.87 (12H, t, J=6.6 Hz)

Example 12

Preparation of pentaerythritol glycolic ester ethoxylate stearyl ether (pentaerythritol steareth-4 carboxylate)

Except that 173.6 g (400 mmol) of glycolic ethoxylate stearyl ether (steareth-4 carboxylic acid) was used instead of glycolic ethoxylate hexyl ether (hexeth-4 carboxylic acid), the same procedure described in Example 1 was performed to obtain 151.1 g of pentaerythritol glycolic ester ethoxylate stearyl ether (pentaerythritol steareth-4 carboxylate).

$^1$H-NMR (in CHCl$_3$): 4.17 (16H), 3.68 (48H), 3.47 (8H, t, J=6.9 Hz), 1.57 (8H, m), 1.26 (120H), 0.88 (12H, t, J=6.6 Hz)

Example 13

Preparation of pentaerythritol glycolic ester ethoxylate stearyl ether (pentaerythritol steareth-6 carboxylate)

Except that 208.8 g (400 mmol) of glycolic ethoxylate stearyl ether (steareth-6 carboxylic acid) was used instead of glycolic ethoxylate hexyl ether (hexeth-4 carboxylic acid), the same procedure described in Example 1 was performed to obtain 183.6 g of pentaerythritol glycolic ester ethoxylate stearyl ether (pentaerythritol steareth-6 carboxylate).

$^1$H-NMR (in CHCl$_3$): 4.17 (16H), 3.67 (80H), 3.47 (8H, t, J=6.6 Hz), 1.57 (8H, m), 1.26 (120H), 0.87 (12H, t, J=6.6 Hz)

Example 14

Preparation of pentaerythritol glycolic ester ethoxylate stearyl ether (pentaerythritol steareth-10 carboxylate)

Except that 279.2 g (400 mmol) of glycolic ethoxylate stearyl ether (steareth-10 carboxylic acid) was used instead of glycolic ethoxylate hexyl ether (hexeth-4 carboxylic acid), the same procedure described in Example 1 was performed to obtain 238.1 g of pentaerythritol glycolic ester ethoxylate stearyl ether (pentaerythritol steareth-10 carboxylate).

$^1$H-NMR (in CHCl$_3$): 4.17 (16H), 3.67 (144H), 3.47 (8H, t, J=6.9 Hz), 1.58 (8H, m), 1.26 (120H), 0.88 (12H, t, J=6.6 Hz)

Example 15

Preparation of pentaerythritol ethoxylate (3/4 EO/OH) glycolic ester ethoxylate hexyl ether (pentaerythritol ethoxylate (3/4 EO/OH) hexeth-4 carboxylate)

Except that 27.0 g (100 mmol) of pentaerythritol ethoxylate (3/4 EO/OH) was used instead of pentaerythritol, the same procedure described in Example 1 was performed to obtain 136.5 g of pentaerythritol ethoxylate (3/4 EO/OH) glycolic ester ethoxylate hexyl ether (pentaerythritol ethoxylate (3/4 EO/OH) hexeth-4 carboxylate).

Example 16

Preparation of pentaerythritol ethoxylate (3/4 EO/OH) glycolic ester ethoxylate hexyl ether (pentaerythritol ethoxylate (3/4 EO/OH hexeth-6 carboxylate)

Except that 27.0 g (100 mmol) of pentaerythritol ethoxylate (3/4 EO/OH) was used instead of pentaerythritol, the same procedure described in Example 2 was performed to obtain 137.1 g of pentaerythritol ethoxylate (3/4 EO/OH) glycolic ester ethoxylate hexyl ether (pentaerythritol ethoxylate (3/4 EO/OH) hexeth-6 carboxylate).

$^1$H-NMR (in CHCl$_3$): 4.18 (16H), 3.66 (92H), 3.44 (8H, t, J=6.9 Hz), 1.57 (8H, m), 1.26 (24H), 0.88 (12H, t, J=6.6 Hz)

Example 17

Preparation of pentaerythritol ethoxylate (3/4 EO/OH) glycolic ester ethoxylate octyl ether(pentaerythritol ethoxylate (3/4 EO/OH) capreth-4 carboxylate)

Except that 27.0 g (100 mmol) of pentaerythritol ethoxylate (3/4 EO/OH) was used instead of pentaerythritol, the same procedure described in Example 3 was performed to obtain 119.9 g of pentaerythritol ethoxylate(3/4 EO/OH) glycolic ester ethoxylate octyl ether (pentaerythritol ethoxylate (3/4 EO/OH) capreth-4 carboxylate).

$^1$H-NMR (in CHCl$_3$): 4.17 (16H), 3.66 (60H), 3.45 (8H, t, J=6.9 Hz), 1.57 (8H, m), 1.26 (40H), 0.87 (12H, t, J=6.6 Hz)

Example 18

Preparation of pentaerythritol ethoxylate (3/4 EO/OH) glycolic ester ethoxylate octyl ether (pentaerythritol ethoxylate (3/4 EO/OH) capreth-6 carboxylate)

Except that 27.0 g (100 mmol) of pentaerythritol ethoxylate (3/4 EO/OH) was used instead of pentaerythritol, the same procedure described in Example 4 was performed to obtain 153.1 g of pentaerythritol ethoxylate (3/4 EO/OH) glycolic ester ethoxylate octyl ether (pentaerythritol ethoxylate (3/4 EO/OH) capreth-6 carboxylate).

$^1$H-NMR (in CHCl$_3$): 4.17 (16H), 3.67 (92H), 3.46 (8H, t, J=6.9 Hz), 1.57 (8H, m), 1.26 (40H), 0.88 (12H, t, J=6.6 Hz)

Example 19

Preparation of pentaerythritol ethoxylate (3/4 EO/OH) glycolic ester ethoxylate lauryl ether (pentaerythritol ethoxylate (3/4 EO/OH) laureth-4 carboxylate)

Except that 27.0 g (100 mmol) of pentaerythritol ethoxylate (3/4 EO/OH) was used instead of pentaerythritol, the same procedure described in Example 5 was performed to obtain 136.8 g of pentaerythritol ethoxylate (3/4 EO/OH) glycolic ester ethoxylate lauryl ether (pentaerythritol ethoxylate (3/4 EO/OH) laureth-4 carboxylate).

$^1$H-NMR (in CHCl$_3$): 4.17 (16H), 3.66 (60H), 3.47 (8H, t, J=6.9 Hz), 1.57 (8H, m), 1.26 (72H), 0.88 (12H, t, J=6.6 Hz)

Example 20

Preparation of pentaerythritol ethoxylate (3/4 EO/OH) glycolic ester ethoxylate lauryl ether (pentaerythritol ethoxylate (3/4 EO/OH) laureth-6 carboxylate)

Except that 27.0 g (100 mmol) of pentaerythritol ethoxylate (3/4 EO/OH) was used instead of pentaerythritol, the same procedure described in Example 6 was performed to obtain 164.2 g of pentaerythritol ethoxylate (3/4 EO/OH) glycolic ester ethoxylate lauryl ether (pentaerythritol ethoxylate (3/4 EO/OH) laureth-6 carboxylate).

$^1$H-NMR (in CHCl$_3$): 4.16 (16H), 3.66 (92H), 3.47 (8H, t, J=6.9 Hz), 1.57 (8H, m), 1.26 (72H), 0.89 (12H, t, J=6.6 Hz)

Example 21

Preparation of pentaerythritol ethoxylate (3/4 EO/OH) glycolic ester ethoxylate lauryl ether (pentaerythritol ethoxylate (3/4 EO/OH) laureth-10 carboxylate)

Except that 27.0 g (100 mmol) of pentaerythritol ethoxylate (3/4 EO/OH) was used instead of pentaerythritol, the same procedure described in Example 7 was performed to obtain 234.1 g of pentaerythritol ethoxylate (3/4 EO/OH) glycolic ester ethoxylate lauryl ether (pentaerythritol ethoxylate (3/4 EO/OH) laureth-10 carboxylate).

$^1$H-NMR (in CHCl$_3$): 4.17 (16H), 3.67 (156H), 3.47 (8H, t, J=6.9 Hz), 1.57 (8H, m), 1.27 (72H), 0.88 (12H, t, J=6.6 Hz)

Example 22

Preparation of pentaerythritol ethoxylate (3/4 EO/OH) glycolic ester ethoxylate cetyl ether (pentaerythritol ethoxylate (3/4 EO/OH) ceteth-4 carboxylate)

Except that 27.0 g (100 mmol) of pentaerythritol ethoxylate (3/4 EO/OH) was used instead of pentaerythritol, the same procedure described in Example 8 was performed to obtain 148.9 g of pentaerythritol ethoxylate (3/4 EO/OH) glycolic ester ethoxylate cetyl ether(pentaerythritol ethoxylate (3/4 EO/OH) ceteth-4 carboxylate).

$^1$H-NMR (in CHCl$_3$): 4.17 (16H), 3.67 (60H), 3.47 (8H, t, J=6.6 Hz), 1.57 (8H, m), 1.27 (104H), 0.88 (12H, t, J=6.6 Hz)

Example 23

Preparation of pentaerythritol ethoxylate(3/4 EO/OH) glycolic ester ethoxylate cetyl ether(pentaerythritol ethoxylate(3/4 EO/OH) ceteth-6 carboxylate)

Except that 27.0 g (100 mmol) of pentaerythritol ethoxylate (3/4 EO/OH) was used instead of pentaerythritol, the same procedure described in Example 9 was performed to obtain 174.8 g of pentaerythritol ethoxylate (3/4 EO/OH) glycolic ester ethoxylate cetyl ether (pentaerythritol ethoxylate (3/4 EO/OH) ceteth-6 carboxylate).

¹H-NMR (in CHCl₃): 4.17 (16H), 3.67 (92H), 3.47 (8H, t, J=6.9 Hz), 1.56 (8H, m), 1.26 (104H), 0.87 (12H, t, J=6.6 Hz)

Example 24

Preparation of pentaerythritol ethoxylate 3/4 EO/OH) glycolic ester ethoxylate cetyl ether (pentaerythritol ethoxylate (3/4 EO/OH) ceteth-10 carboxylate)

Except that 27.0 g (100 mmol) of pentaerythritol ethoxylate (3/4 EO/OH) was used instead of pentaerythritol, the same procedure described in Example 10 was performed to obtain 259.0 g of pentaerythritol ethoxylate (3/4 EO/OH) glycolic ester ethoxylate cetyl ether (pentaerythritol ethoxylate (3/4 EO/OH) ceteth-10 carboxylate).
¹H-NMR (in CHCl₃): 4.18 (16H), 3.67 (156H), 3.47 (8H, t, J=6.9 Hz), 1.57 (8H, m), 1.26 (104H), 0.87 (12H, t, J=6.6 Hz)

Example 25

Preparation of pentaerythritol ethoxylate (3/4 EO/OH) glycolic ester ethoxylate oleyl ether (pentaerythritol ethoxylate (3/4 EO/OH) oleth-6 carboxylate)

Except that 27.0 g (100 mmol) of pentaerythritol ethoxylate (3/4 EO/OH) was used instead of pentaerythritol, the same procedure described in Example 11 was performed to obtain 208.7 g of pentaerythritol ethoxylate (3/4 EO/OH) glycolic ester ethoxylate oleyl ether (pentaerythritol ethoxylate (3/4 EO/OH) oleth-6 carboxylate).
¹H-NMR (in CHCl₃): 5.64 (8H), 4.17 (16H), 3.67 (92H), 3.47 (8H, t, J=6.9 Hz), 2.01 (16H), 1.57 (8H, m), 1.27 (80H), 0.88 (12H, t, J=6.6 Hz)

Example 26

Preparation of pentaerythritol ethoxylate (3/4 EO/OH) glycolic ester ethoxylate stearyl ether (pentaerythritol ethoxylate (3/4 EO/OH) steareth-4 carboxylate)

Except that 27.0 g (100 mmol) of pentaerythritol ethoxylate (3/4 EO/OH) was used instead of pentaerythritol, the same procedure described in Example 12 was performed to obtain 159.1 g of pentaerythritol ethoxylate (3/4 EO/OH) glycolic ester ethoxylate stearyl ether (pentaerythritol ethoxylate (3/4 EO/OH) steareth-4 carboxylate).
¹H-NMR (in CHCl₃): 4.17 (16H), 3.68 (60H), 3.47 (8H, t, J=6.9 Hz), 1.57 (8H, m), 1.27 (120H), 0.87 (12H, t, J=6.6 Hz)

Example 27

Preparation of pentaerythritol ethoxylate (3/4 EO/OH) glycolic ester ethoxylate stearyl ether (pentaerythritol ethoxylate (3/4 EO/OH) steareth-6 carboxylate)

Except that 27.0 g (100 mmol) of pentaerythritol ethoxylate (3/4 EO/OH) was used instead of pentaerythritol, the same procedure described in Example 13 was performed to obtain 194.8 g of pentaerythritol ethoxylate (3/4 EO/OH) glycolic ester ethoxylate stearyl ether (pentaerythritol ethoxylate (3/4 EO/OH) steareth-6 carboxylate).
¹H-NMR (in CHCl₃): 4.17 (16H), 3.67 (92H), 3.47 (8H, t, J=6.6 Hz), 1.57 (8H, m), 1.27 (120H), 0.87 (12H, t, J=6.6 Hz)

Example 28

Preparation of pentaerythritol ethoxylate (3/4 EO/OH) glycolic ester ethoxylate stearyl ether (pentaerythritol ethoxylate (3/4 EO/OH) steareth-10 carboxylate)

Except that 27.0 g (100 mmol) of pentaerythritol ethoxylate (3/4 EO/OH) was used instead of pentaerythritol, the same procedure described in Example 14 was performed to obtain 250.7 g of pentaerythritol ethoxylate (3/4 EO/OH) glycolic ester ethoxylate stearyl ether (pentaerythritol ethoxylate (3/4 EO/OH) steareth-10 carboxylate).
¹H-NMR (in CHCl₃): 4.17 (16H), 3.67 (156H), 3.47 (8H, t, J=6.9 Hz), 1.58 (8H, m), 1.26 (120H), 0.88 (12H, t, J=6.6 Hz)

Example 29

Preparation of pentaerythritol ethoxylate (15/4 EO/OH) glycolic ester ethoxylate hexyl ether (pentaerythritol ethoxylate (15/4 EO/OH) hexeth-4 carboxylate)

Except that 79.7 g (100 mmol) of pentaerythritol ethoxylate (15/4 EO/OH) was used instead of pentaerythritol, the same procedure described in Example 1 was performed to obtain 183.5 g of pentaerythritol ethoxylate (15/4 EO/OH) glycolic ester ethoxylate hexyl ether (pentaerythritol ethoxylate (15/4 EO/OH) hexeth-4 carboxylate).
¹H-NMR (in CHCl₃): 4.17 (16H), 3.67 (108H), 3.43 (8H, t, J=6.9 Hz), 1.56 (8H, m), 1.26 (24H), 0.88 (12H, t, J=6.6 Hz)

Example 30

Preparation of pentaerythritol ethoxylate (15/4 EO/OH) glycolic ester ethoxylate hexyl ether (pentaerythritol ethoxylate (15/4 EO/OH) hexeth-6 carboxylate)

Except that 79.7 g (100 mmol) of pentaerythritol ethoxylate(15/4 EO/OH) was used instead of pentaerythritol, the same procedure described in Example 2 was performed to obtain 187.1 g of pentaerythritol ethoxylate(15/4 EO/OH) glycolic ester ethoxylate hexyl ether(pentaerythritol ethoxylate(15/4 EO/OH) hexeth-6 carboxylate).
¹H-NMR (in CHCl₃): 4.18 (16H), 3.66 (140H), 3.44 (8H, t, J=6.9 Hz), 1.56 (8H, m), 1.26 (24H), 0.88 (12H, t, J=6.6 Hz)

Example 31

Preparation of pentaerythritol ethoxylate (15/4 EO/OH) glycolic ester ethoxylate octyl ether (pentaerythritol ethoxylate (15/4 EO/OH) capreth-4 carboxylate)

Except that 79.7 g (100 mmol) of pentaerythritol ethoxylate (15/4 EO/OH) was used instead of pentaerythritol, the same procedure described in Example 3 was performed to obtain 170.2 g of pentaerythritol ethoxylate (15/4 EO/OH) glycolic ester ethoxylate octyl ether (pentaerythritol ethoxylate (15/4 EO/OH) capreth-4 carboxylate).
¹H-NMR (in CHCl₃): 4.17 (16H), 3.66 (108H), 3.45 (8H, t, J=6.9 Hz), 1.57 (8H, m), 1.26 (40H), 0.88 (12H, t, J=6.6 Hz)

Example 32

Preparation of pentaerythritol ethoxylate (15/4 EO/OH) glycolic ester ethoxylate octyl ether (pentaerythritol ethoxylate (15/4 EO/OH) capreth-6 carboxylate)

Except that 79.7 g (100 mmol) of pentaerythritol ethoxylate (15/4 EO/OH) was used instead of pentaerythritol, the same procedure described in Example 4 was performed to obtain 201.1 g of pentaerythritol ethoxylate (15/4 EO/OH) glycolic ester ethoxylate octyl ether (pentaerythritol ethoxylate (15/4 EO/OH) capreth-6 carboxylate).

$^1$H-NMR (in CHCl$_3$): 4.17 (16H), 3.67 (140H), 3.47 (8H, t, 0.1=6.9 Hz), 1.56 (8H, m), 1.26 (40H), 0.88 (12H, t, J=6.6 Hz)

Example 33

Preparation of pentaerythritol ethoxylate (15/4 EO/OH) glycolic ester ethoxylate lauryl ether (pentaerythritol ethoxylate (15/4 EO/OH) laureth-4 carboxylate)

Except that 79.7 g (100 mmol) of pentaerythritol ethoxylate (15/4 EO/OH) was used instead of pentaerythritol, the same procedure in Example 5 was performed to obtain 188.8 g of pentaerythritol ethoxylate (15/4 EO/OH) glycolic ester ethoxylate lauryl ether (pentaerythritol ethoxylate (15/4 EO/OH) laureth-4 carboxylate).

$^1$H-NMR (in CHCl$_3$): 4.16 (16H), 3.66 (108H), 3.47 (8H, t, J=6.9 Hz), 1.57 (8H, m), 1.26 (72H), 0.88 (12H, t, J=6.6 Hz)

Example 34

Preparation of pentaerythritol ethoxylate (15/4 EO/OH) glycolic ester ethoxylate lauryl ether (pentaerythritol ethoxylate (15/4 EO/OH) laureth-6 carboxylate)

Except that 79.7 g (100 mmol) of pentaerythritol ethoxylate (15/4 EO/OH) was used instead of pentaerythritol, the same procedure in Example 6 was performed to obtain 213.7 g of pentaerythritol ethoxylate (15/4 EO/OH) glycolic ester ethoxylate lauryl ether (pentaerythritol ethoxylate (15/4 EO/OH) laureth-6 carboxylate).

$^1$H-NMR (in CHCl$_3$): 4.16 (16H), 3.66 (140H), 3.46 (8H, t, J=6.9 Hz), 1.57 (8H, m), 1.26 (72H), 0.89 (12H, t, J=6.6 Hz)

Example 35

Preparation of pentaerythritol ethoxylate (15/4 EO/OH) glycolic ester ethoxylate lauryl ether (pentaerythritol ethoxylate (15/4 EO/OH) laureth-10 carboxylate)

Except that 79.7 g (100 mmol) of pentaerythritol ethoxylate (15/4 EO/OH) was used instead of pentaerythritol, the same procedure described in Example 7 was performed to obtain 286.3 g of pentaerythritol ethoxylate (15/4 EO/OH) glycolic ester ethoxylate lauryl ether (pentaerythritol ethoxylate (15/4 EO/OH) laureth-10 carboxylate).

$^1$H-NMR (in CHCl$_3$): 4.17 (16H), 3.67 (204H), 3.47 (8H, t, J=6.9 Hz), 1.57 (8H, m), 1.28 (72H), 0.88 (12H, t, J=6.6 Hz)

Example 36

Preparation of pentaerythritol ethoxylate (15/4 EO/OH) glycolic ester ethoxylate cetyl ether (pentaerythritol ethoxylate (15/4 EO/OH) ceteth-4 carboxylate)

Except that 79.7 g (100 mmol) of pentaerythritol ethoxylate (15/4 EO/OH) was used instead of pentaerythritol, the same procedure described in Example 8 was performed to obtain 199.3 g of pentaerythritol ethoxylate (15/4 EO/OH) glycolic ester ethoxylate cetyl ether (pentaerythritol ethoxylate (15/4 EO/OH) ceteth-4 carboxylate).

$^1$H-NMR (in CHCl$_3$): 4.17 (16H), 3.66 (108H), 3.47 (811, t, J=6.6 Hz), 1.57 (8H, m), 1.27 (104H), 0.88 (12H, t, J=6.6 Hz)

Example 37

Preparation of pentaerythritol ethoxylate (15/4 EO/OH) glycolic ester ethoxylate cetyl ether (pentaerythritol ethoxylate (15/4 EO/OH) ceteth-6 carboxylate)

Except that 79.7 g (100 mmol) of pentaerythritol ethoxylate (15/4 EO/OH) was used instead of pentaerythritol, the same procedure described in Example 9 was performed to obtain 224.8 g of pentaerythritol ethoxylate (15/4 EO/OH) glycolic ester ethoxylate cetyl ether (pentaerythritol ethoxylate (15/4 EO/OH) ceteth-6 carboxylate).

$^1$H-NMR (in CHCl$_3$): 4.17 (16H), 3.67 (140H), 3.46 (8H, t, J=6.9 Hz), 1.56 (8H, m), 1.26 (104H), 0.87 (12H, t, J=6.6 Hz)

Example 38

Preparation of pentaerythritol ethoxylate (15/4 EO/OH) glycolic ester ethoxylate cetyl ether (pentaerythritol ethoxylate (15/4 EO/OH) ceteth-10 carboxylate)

Except that 79.7 g (100 mmol) of pentaerythritol ethoxylate (15/4 EO/OH) was used instead of pentaerythritol, the same procedure described in Example 10 was performed to obtain 301.2 g of pentaerythritol ethoxylate (15/4 EO/OH) glycolic ester ethoxylate cetyl ether (pentaerythritol ethoxylate (15/4 EO/OH) ceteth-10 carboxylate).

$^1$H-NMR (in CHCl$_3$): 4.18 (16H), 3.67 (204H), 3.47 (8H, t, J=6.9 Hz), 1.57 (8H, m), 1.27 (104H), 0.89 (12H, t, J=6.6 Hz)

Example 39

Preparation of pentaerythritol ethoxylate (15/4 EO/OH) glycolic ester ethoxylate oleyl ether (pentaerythritol ethoxylate (15/4 EO/OH) oleth-6 carboxylate)

Except that 79.7 g (100 mmol) of pentaerythritol ethoxylate (15/4 EO/OH) was used instead of pentaerythritol, the same procedure described in Example 11 was performed to obtain 290.4 g of pentaerythritol ethoxylate (15/4 EO/OH) glycolic ester ethoxylate oleyl ether (pentaerythritol ethoxylate (15/4 EO/OH) oleth-6 carboxylate).

¹H-NMR (in CHCl₃): 5.63 (8H), 4.16 (16H), 3.67 (140H), 3.48 (8H, t, J=6.9 Hz), 2.02 (16H), 1.57 (8H, m), 1.27 (80H), 0.87 (12H, t, J=6.6 Hz)

Example 40

Preparation of pentaerythritol ethoxylate (15/4 EO/OH) glycolic ester ethoxylate stearyl ether (pentaerythritol ethoxylate (15/4 EO/OH) steareth-4 carboxylate)

Except that 79.7 g (100 mmol) of pentaerythritol ethoxylate (15/4 EO/OH) was used instead of pentaerythritol, the same procedure described in Example 12 was performed to obtain 220.0 g of pentaerythritol ethoxylate (15/4 EO/OH) glycolic ester ethoxylate stearyl ether (pentaerythritol ethoxylate (15/4 EO/OH) steareth-4 carboxylate).

¹H-NMR (in CHCl₃): 4.17 (16H), 3.68 (108H), 3.47 (8H, t, J=6.9 Hz), 1.57 (8H, m), 1.27 (120H), 0.87 (12H, t, J=6.6 Hz)

Example 41

Preparation of pentaerythritol ethoxylate (15/4 EO/OH) glycolic ester ethoxylate stearyl ether (pentaerythritol ethoxylate (15/4 EO/OH) steareth-6 carboxylate)

Except that 79.7 g (100 mmol) of pentaerythritol ethoxylate(15/4 EO/OH) was used instead of pentaerythritol, the same procedure described in Example 13 was performed to obtain 241.3 g of pentaerythritol ethoxylate (15/4 EO/OH) glycolic ester ethoxylate stearyl ether (pentaerythritol ethoxylate (15/4 EO/OH) steareth-6 carboxylate).

¹H-NMR (in CHCl₃): 4.17 (16H), 3.67 (140H), 3.47 (8H, t, J=6.6 Hz), 1.57 (8H, m), 1.27 (120H), 0.87 (12H, t, J=6.6 Hz)

Example 42

Preparation of pentaerythritol ethoxylate (15/4 EO/OH) glycolic ester ethoxylate stearyl ether (pentaerythritol ethoxylate (15/4 EO/OH) steareth-10 carboxylate)

Except that 79.7 g (100 mmol) of pentaerythritol ethoxylate (15/4 EO/OH) was used instead of pentaerythritol, the same procedure described in Example 14 was performed to obtain 300.7 g of pentaerythritol ethoxylate (15/4 EO/OH) glycolic ester ethoxylate stearyl ether (pentaerythritol ethoxylate (15/4 EO/OH) steareth-10 carboxylate).

¹H-NMR (in CHCl₃): 4.17 (16H), 3.67 (204H), 3.47 (8H, t, J=6.9 Hz), 1.57 (8H, m), 1.26 (120H), 0.88 (12H, t, J=6.6 Hz)

Experimental Example 1

Evaluation of the Increase of Moisture Content in the Skin

The degree of the increase of moisture content in the skin was measured for the compounds obtained in the Examples. The increase of moisture content in the skin was measured by dividing 50 hairless Guinea pigs into 10 groups, and applying the compounds obtained in the Examples to each group.

Specifically, after the skin barrier was damaged by patching acetone using Finn chamber for 30 minutes to the flank site of the experiment animals, 200 μl of each experimental substance was applied to the patched site, then the moisture content of the stratum corneum of the site was measured using Corneometer and then evaluated. Apparatus measurements were carried out directly after and 6 hours, 12 hours, 24 hours and 48 hours after removing the acetone patch. Changes of moisture content in the skin were evaluated relative to the content measured directly after the acetone treatment, which was set to be 100. The results are shown in the following table 1.

TABLE 1

| Compound | | Directly after acetone treatment | After sample application | | | |
|---|---|---|---|---|---|---|
| | | | 6 h | 12 h | 24 h | 48 h |
| Vehicle (PG:EtOH = 7:3) | | 100 | 98 | 95 | 93 | 86 |
| Glycerol | | 100 | 109 | 113 | 115 | 117 |
| Example No. | 5 | 100 | 98 | 99 | 103 | 105 |
| | 10 | 100 | 101 | 105 | 109 | 113 |
| | 17 | 100 | 103 | 106 | 108 | 104 |
| | 22 | 100 | 100 | 105 | 109 | 115 |
| | 29 | 100 | 106 | 109 | 111 | 109 |
| | 34 | 100 | 105 | 110 | 116 | 114 |
| | 38 | 100 | 108 | 111 | 112 | 114 |
| | 42 | 100 | 106 | 110 | 109 | 111 |

As shown in table 1, pentaerythritol derivatives of the present invention showed the effect of increasing moisture content inside the skin compared with the vehicle (propylene glycol:ethanol=7:3), and showed a similar effect to glycerol.

Experimental Example 2

Evaluation of Moisture Retaining Ability in Dry Conditions

Moisture retaining ability was evaluated and compared for the compounds obtained in the Examples.

Specifically, samples were prepared such that the moisture content of the compounds obtained in the Examples was 60%, and while the samples were kept in a constant temperature and humidity chamber (18° C., RH 20%), the weight change of the samples was observed over time, thereby enabling evaluation of the changes in moisture content. The results are shown in the following table 2.

TABLE 2

| Compound | | Initial | 1 h | 2 h | 4 h | 6 h |
|---|---|---|---|---|---|---|
| Vehicle (PG:EtOH = 7:3) | | 60 | 54 | 46 | 35 | 21 |
| Glycerol | | 60 | 57 | 50 | 41 | 25 |
| Example No. | 5 | 60 | 58 | 55 | 49 | 41 |
| | 10 | 60 | 58 | 57 | 50 | 44 |
| | 17 | 60 | 57 | 53 | 47 | 38 |
| | 22 | 60 | 56 | 52 | 48 | 43 |
| | 29 | 60 | 57 | 55 | 50 | 43 |
| | 34 | 60 | 58 | 56 | 49 | 45 |
| | 38 | 60 | 58 | 52 | 44 | 29 |
| | 42 | 60 | 57 | 55 | 48 | 34 |

As shown in Table 2 above, pentaerythritol derivatives of the present invention showed high moisture retaining ability compared with the vehicle (propylene glycol:ethanol=7:3) and glycerol.

From the above results of Experimental Examples 1 and 2, it was found that pentaerythritol derivatives provided by the present invention are able to improve moisture retaining ability of the stratum corneum when applied to the skin, and especially they show high moisturizing ability even in dry conditions. Therefore, the cosmetic compositions comprising the pentaerythritol derivatives of the present invention provide long lasting moisture together with high moisturizing ability, and especially a high moisturizing effect even in dry conditions.

In the below Preparation Examples and Experimental Example 3, liquid crystal bases containing pentaerythritol derivatives of the present invention were prepared, to evaluate the stability of liquid crystal base.

Preparation Examples 1~24

Preparation of Liquid Crystal Base

Liquid crystal bases containing pentaerythritol derivatives obtained in the Examples were prepared. Liquid crystal bases were prepared by combining pentaerythritol derivative of the present invention, fatty acid and cholesterol in a proper composition on a basis of analytic condition of lipid. The type of fatty acids used and the content of each component are shown in the following table 3.

TABLE 3

| Preparation Example | Pentaerythritol derivatives Type | Content | Fatty acid Type | Content | Cholesterol Content |
|---|---|---|---|---|---|
| 1 | Ex. 10 | 33.3 | Stearic acid | 33.3 | 33.3 |
| 2 | | 33.3 | Palmitic acid | 33.3 | 33.3 |
| 3 | | 39 | Stearic acid | 28 | 33 |
| 4 | | 39 | Palmitic acid | 28 | 33 |
| 5 | | 52 | Stearic acid | 16 | 32 |
| 6 | | 52 | Palmitic acid | 16 | 32 |
| 7 | Ex. 22 | 33.3 | Stearic acid | 33.3 | 33.3 |
| 8 | | 33.3 | Palmitic acid | 33.3 | 33.3 |
| 9 | | 39 | Stearic acid | 28 | 33 |
| 10 | | 39 | Palmitic acid | 28 | 33 |
| 11 | | 52 | Stearic acid | 16 | 32 |
| 12 | | 52 | Palmitic acid | 16 | 32 |
| 13 | Ex. 34 | 33.3 | Stearic acid | 33.3 | 33.3 |
| 14 | | 33.3 | Palmitic acid | 33.3 | 33.3 |
| 15 | | 39 | Stearic acid | 28 | 33 |
| 16 | | 39 | Palmitic acid | 28 | 33 |
| 17 | | 52 | Stearic acid | 16 | 32 |
| 18 | | 52 | Palmitic acid | 16 | 32 |
| 19 | Ex. 42 | 33.3 | Stearic acid | 33.3 | 33.3 |
| 20 | | 33.3 | Palmitic acid | 33.3 | 33.3 |
| 21 | | 39 | Stearic acid | 28 | 33 |
| 22 | | 39 | Palmitic acid | 28 | 33 |
| 23 | | 52 | Stearic acid | 16 | 32 |
| 24 | | 52 | Palmitic acid | 16 | 32 |

Experimental Example 3

Evaluation of the Liquid Crystal Formability of Liquid Crystal Base

Figure 1:
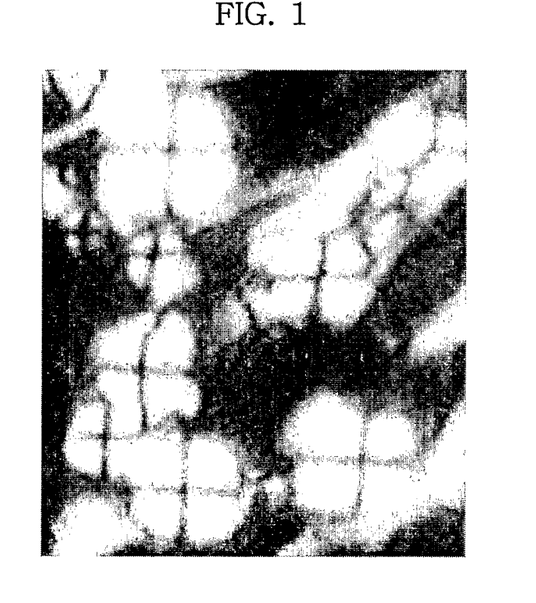
FIG. 1 shows the liquid crystal base of Preparation Example 3 observed by polarizing microscope.
Figure 2:
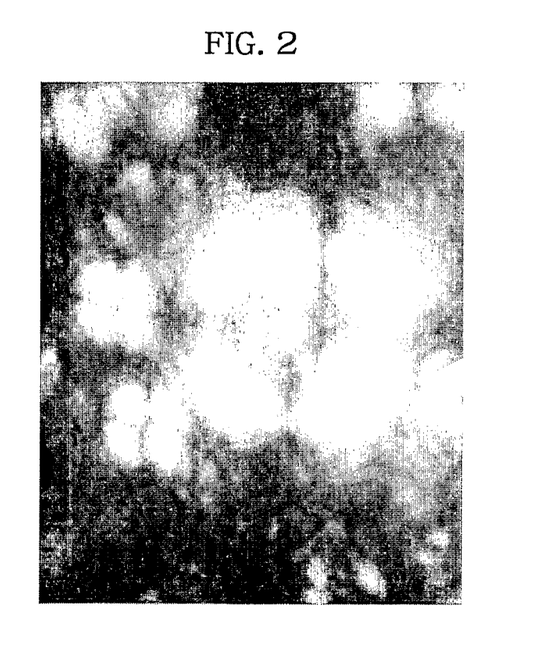
FIG. 2 shows the liquid crystal base of Preparation Example 8 observed by polarizing microscope.
Figure 3:
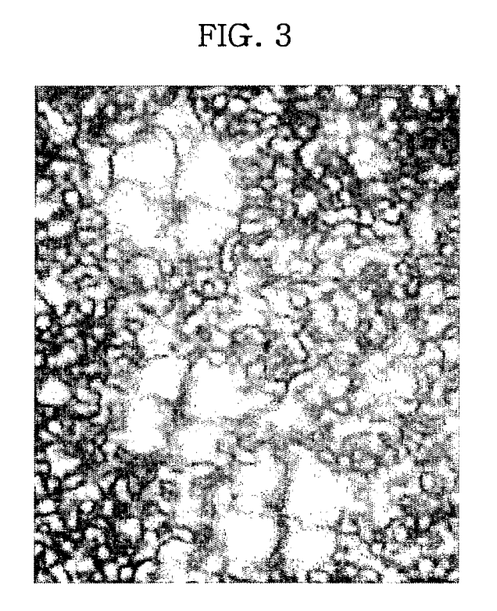
FIG. 3 shows the liquid crystal base of Preparation Example 17 observed by polarizing microscope.
Figure 4:
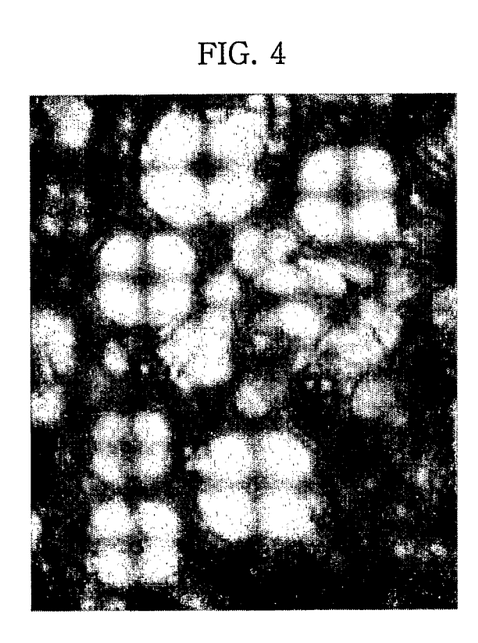
FIG. 4 shows the liquid crystal base of Preparation Example 21 observed by polarizing microscope.

Formation of non-formation of liquid crystal in the liquid crystal bases of Preparation Examples 1~24 was evaluated using polarizing microscope. For most compounds, polarizing results of the typical clover shape of lamella liquid crystal were observed. FIGS. 1 to 4 show the results.

From the above results, it was found that the pentaerythritol derivatives of the present invention can stably form liquid crystal inside a liquid crystal base. The pentaerythritol derivatives of the present invention may be combined in the amount of 10~70% based on the total weight of liquid crystal base.

As described above, the pentaerythritol derivatives according to the present invention and the crystal base containing the same provide long lasting moisture together with high moisturizing ability, and especially a high moisturizing effect even in dry conditions. Further, they may be usefully combined in skin moisturizing cosmetic compositions.

Hereinbefore, the present invention was illustrated through preferred embodiments, which may be varied by those skilled in the art within the extent of the technical spirit and scope of the present invention.

The invention claimed is:

1. A skin moisturizer comprising a pentaerythritol compound represented by the following Formula 1:

Formula 1 wherein R is independently saturated or unsaturated C6-C18 alkyl group;

m and n are the same or different from each other, wherein m is 0 or an integer of 1 to 10 and n is an integer of 1 to 10, and wherein the compound of Formula 1 is selected from the group of pentaerythritol hexeth-4 carboxylate, pentaerythritol hexeth-6 carboxylate, pentaerythritol capreth-4 carboxylate, pentaerythritol capreth-6 carboxylate, pentaerythritol laureth-4 carboxylate, pentaerythritol laureth-6 carboxylate, pentaervthritol laureth-10 carboxylate, pentaerythritol ceteth-4 carboxlate, pentaerythritol ceteth-6-carboxlyate, pentaerythritol ceteth-10 carboxylate pentaethritol oleth-6 carboxylate, pentaethritol steareth-4 carboxylate, pentaethritol steareth-6 carboxylate, pentaerythritol steareth-10 carboxylate, pentaerythritol ethoxylate (3/4 EO/OH) hexeth-4 carboxylate, pentaerythritol ethoxylate (3/4 EO/OH) hexeth-6 carboxylate, pentaethritol ethoxylate 3/4 EO/OH) capreth-4 carboxylate, pentaethritol ethoxylate 3/4 EO/OH) capreth-6 carboxylate, pentaerythritol ethoxylate (3/4 EO/OH) laureth-4 carboxylate, pentaerythritol ethoxylate (3/4 EO/OH) laureth-6 carboxylate, pentaerythritol ethoxylate (3/4 EO/OH) laureth-10 carboxylate, pentaerythritol ethoxylate (3/4 EO/OH) ceteth-4 carboxylate, pentaethritol ethoxylate 3/4 EO/OH) ceteth-6 carboxylate, pentaethritol ethoxylate 3/4 EO/OH) ceteth-10 carboxylate, pentaerythritol ethoxylate (3/4 EO/OH) oleth-6 carboxylate, pentaerythritol ethoxylate (3/4 EO/OH) steareth-4 carboxylate, pentaerythritol ethoxylate (3/4 EO/OH) steareth-6 carboxylate, pentaerythritol ethoxylate (3/4 EO/OH) steareth-10 carboxylate, pentaerythritol ethoxylate (15/4 EO/OH) hexeth-4 carboxylate, pentaethritol ethoxylate (15/4 EO/OH) hexeth-6 carboxylate, pentaethritol ethoxylate 15/4 EO/OH) capreth-4 carboxylate, pentaerythritol ethoxylate (15/4 EO/OH) capreth-6 carboxylate, pentaerythritol ethoxylate (15/4 EO/OH) laureth-4 carboxylate, pentaethritol ethoxylate (15/4 EO/OH) laureth-6 carboxylate, pentaethritol ethoxylate (15/4 EO/OH) laureth-10 carboxylate, pentaethritol ethoxylate (15/4 EO/OH) ceteth-4 carboxylate, pentaerythritol ethoxylate (15/4 EO/OH) ceteth-6 carboxylate, pentaerythritol ethoxylate (15/4 EO/OH) ceteth-10 carboxylate, pentaerythritol ethoxylate (15/4 EO/OH) oleth-6 carboxylate, pentaerythritol ethoxylate (15/4 EO/OH) steareth-4 carboxylate, pentaerythritol ethoxylate (15/4 EO/OH) steareth-6 carboxylate, and pentaerythritol ethoxylate (15/4 EO/OH) steareth-10 carboxylate.

* * * * *